(12) United States Patent
Patil (10) Patent No.: US 6,238,575 B1
(45) Date of Patent: May 29, 2001

(54) ANTIMICROBIAL TREATMENT OF ENCLOSED SYSTEMS HAVING CONTINUOUS OR INTERMITTENT FLUID FLOW

(75) Inventor: Arvind S. Patil, Davidson, NC (US)

(73) Assignee: Microban Products Company, Huntersville, NC (US)

( * ) Notice: Subject to any disclaimer, the term of this patent is extended or adjusted under 35 U.S.C. 154(b) by 0 days.

(21) Appl. No.: 09/362,619

(22) Filed: Jul. 28, 1999

Related U.S. Application Data
(60) Provisional application No. 60/094,532, filed on Jul. 29, 1998.

(51) Int. Cl.[7] ............................................. C02F 1/50
(52) U.S. Cl. ......................... 210/764; 210/167; 210/193; 424/411
(58) Field of Search ........................... 210/753, 754, 210/755, 764, 167, 193, 198.1; 424/411

(56) References Cited

U.S. PATENT DOCUMENTS 4,933,178 * 6/1990 Capelli .
5,204,004 * 4/1993 Johnston et al. .
5,817,325 * 10/1998 Sawan et al. ........................ 424/411
5,919,554 * 7/1999 Watterson, III et al. .

* cited by examiner

*Primary Examiner*—Duane Smith
*Assistant Examiner*—Betsey Morrison Hoey
(74) *Attorney, Agent, or Firm*—Dougherty & Clements LLP (57) ABSTRACT

An enclosed fluid system that is resistant to the formation of biofilm at any and all points of contact between system components and the fluid stored or transported therethrough. The enclosed fluid system includes a point of fluid entry, such as a pump from a well, and a point of fluid exit, such as a water tap, and is inclusive of the fluid entry and exit. Each of the system components comprise fluid contacting portions that are made of polymers or a polymer composite material. Between the point of fluid entry and the point of fluid exit of the invented enclosed fluid system are various conventional valves, fluid circulation members, such as pipes, filters and fluid storage members, such as water tanks, and fluid treatment filters, such as depths filters, activated carbon filters, reverse osmosis membranes and ion-exchange resins. A non-leaching antimicrobial agent that inhibits the growth of microorganisms is incorporated into the fluid contacting portions of all system components.

14 Claims, 1 Drawing Sheet

ANTIMICROBIAL TREATMENT OF ENCLOSED SYSTEMS HAVING CONTINUOUS OR INTERMITTENT FLUID FLOW

CROSS REFERENCE TO RELATED APPLICATION

This application claims the benefit of U.S. Provisional Application No. 60/094,532 filed on Jul. 29, 1998.

FIELD OF THE INVENTION

The present invention relates generally to enclosed fluid systems having continuous or intermittent fluid flow, and more particularly to enclosed fluid systems having means for resisting contamination by microorganisms.

BACKGROUND OF THE INVENTION

Many industrial and municipal fluid treatment and distribution systems, as well as small fluid systems such as ice machines, water coolers, fruit juice dispensers, and soft drink machines, are "enclosed fluid systems" having continuous or intermittent fluid flow. The term "enclosed fluid system " as used herein is defined as a system in which fluid is stagnant in at least one portion of the total system and in which there is an intermittent or continuous flow of fluid through the system. Such a system includes distribution piping, storage vessels, metering systems, valves, fittings and fitting accessories, attachments, filter housings, and treatment devices that provide locations where stagnant fluid may reside and where nutrients are available for the growth of microorganisms. The term "fluid" as used herein means liquids such as water, water-oil emulsion, sugar syrups, liquid components, fruit juices, beer, wine, ketchup, molasses. In rare cases, the fluid system may be non-aqueous in nature such as saturated or unsaturated partially hydrogenated oils, alcohols, and wines. In any event, the enclosed systems contain a fluid that is subject to the formation of a biofilm.

The unchecked growth of microorganisms in a fluid system leads to the formation of a biofilm within the system. Biofilm is a conglomerate of microorganisms, such as bacteria, fungi and algae, that are held together, in part, by a sticky substance called exopolysaccharide. Bacteria produce exopolysaccharide, or slime, after attachment of the bacteria to a surface within the fluid system. This slime may be 100 or more times the mass of bacterial cells and helps to anchor and protect microorganisms against disinfecting treatments and allow them to proliferate. Microorganisms protected by the biofilm are resistant to disinfection and enter into the fluid, either continuously or intermittently, as the biofilm sloughs off because of the fluid flow or other mechanical perturbances. Thus, biofilm acts as a major source of microorganism contamination in fluid systems. In many municipal water treatment and distribution systems, the formation of a downstream biofilm negates any upstream treatment of water that attempted to remove the heterotrophic or infectious microorganisms.

Typically, an enclosed fluid system having continuous or intermittent fluid flow is constructed using plastic components. For example, tubing and piping may be made from polyolefin, polyvinylidene fluoride, polyvinyl chloride, ethylene vinyl acetate and polyurethane. Tubing or piping made from polyvinylidene fluoride and polyvinyl chloride are commonly used in the transportation and production of high purity water for the pharmaceutical and electronic industries. For example, tubing made from polyvinyl chloride and polyurethane is used in dental chairs to transport water to the patient during dental procedures. Tubing made singly or coextruded with silicone polymers, polyvinyl chloride/nitrile, polyethylene, chlorobutyl, styrene butadiene rubber, nylon or vinyl acetate are used in food and soft drink dispensing machines.

Numerous plastic polymers and copolymers may be used in these enclosed systems, including among others: epoxies, polyethylene, polyurethane, polypropylene, polyvinyl chloride, acrylonitrile butadiene styrene, polystyrene, polycarbonate, polyvinylidene fluoride, polyacrylate, polymethyl methacrylate, isoprene, styrene butadiene rubber, butyl rubber, polyurethane, silicone, polybutylene, polybutylene terephthalate, polyether sulfone, polyphenyllenoxide, polyphenylene ether, polyphenylene sulfide, polyphtatamide, polysulphene, polyester, nylons, fluoropolymers, and other combinations of polymers. Various copolymers as well as physical combinations of the aforementioned polymers and their alloys are also used in enclosed systems. All of the aforementioned plastic polymers, copolymers and combinations thereof are susceptible to formation of biofilms.

Because many enclosed fluid systems require fluid with particular characteristics, for example cold water from a water cooler, incorporation of a fluid storage chamber is often necessary for the enclosed fluid system. Often these fluid storage chambers are made of the aforementioned plastics. However, enclosed systems may also include metallic based containers, transportation systems or devices. These metallic based containers, transportation systems or devices are typically either powder coated with one or more of the above polymeric substances, such as shown in U.S. Pat. No. 5,238,749, or lined with polymeric substances. For example, pressurized or un-pressurized water storage tanks are often used with wells, hot water heaters and reverse osmosis devices. Pressurized tanks commonly have a flexible butyl rubber or polyurethane diaphragm that is coupled with a plastic liner which together are enclosed in a steel tank. The steel tank is provided with inlet and outlet connections for the flow of water into and out of the tank. The space above the diaphragm is pressurized so that a constant flow of water is afforded regardless of the line pressure. While the predominant fluid transported and contained by enclosed fluid systems is water, it should be understood that enclosed fluid systems may be utilized with other water miscible solvents or oil based emulsions. In rare cases, the fluid system could be non-aqueous in nature, such as saturated or unsaturated, partially hydrogenated oils, alcohols and wines, and food slurries. The major consideration is that the enclosed fluid systems containing any fluid are subject to the formation of biofilm or susceptible to contamination by microorganisms.

What is therefore needed is an enclosed fluid system having continuous or intermittent fluid flow that is resistant to contamination by microorganisms. More particularly, a need exists for an enclosed fluid system that is resistant to contamination by microorganisms throughout the system including the fluid input member, the fluid circulation members, fluid storage members and the fluid exit member. Further needed is an enclosed fluid system that is resistant to biofilm formation for the production and transportation of high purity water in pharmaceutical and electronic applications.

OBJECTS OF THE INVENTION

A principal object of the invention is to provide a totally enclosed fluid system that is resistant to the formation of biofilm regardless of continuous or intermittent fluid flow therethrough.

Another object of the invention is to provide a totally enclosed fluid system that is resistant to contamination by microorganisms resulting from the formation of biofilm.

Another object of the invention is to provide a totally enclosed fluid system that is resistant to contamination by microorganisms and that may be used in both residential and commercial settings.

SUMMARY OF THE INVENTION

The present invention is an enclosed fluid system that is resistant to the formation of biofilm at any and all points of contact between system components and the fluid stored or transported therethrough. In a most basic form, the invented enclosed fluid system comprises a fluid entry member having a point of fluid entry, such as a pump from a well, at least one intermediate member and a fluid exit member having a point of fluid exit, such as a water tap, and is inclusive of the fluid entry, intermediate member and exit. In a preferred embodiment, each of the system components comprise fluid contacting portions that are made of polymers or a polymer composite material. Between the point of fluid entry and the point of fluid exit of the invented enclosed fluid system are various conventional valves, fluid circulation members, such as pipes, filters, fluid treatment members and fluid storage members, such as water tanks. In a preferred embodiment of the invention, a non-leaching antimicrobial agent that inhibits the growth of microorganisms is incorporated into the fluid contacting portions of all system components. The term "incorporate" as used herein in relation to antimicrobial agents or additives, is defined to mean residing in the interstitial spaces of the polymeric matrix of the polymeric material. From the point that the fluid enters the system through the point that the fluid exits the system, the fluid is contained within an enclosed space formed by the fluid contacting portions of the invented enclosed fluid system having the antimicrobial agent associated therewith.

DETAILED DESCRIPTION OF THE INVENTION

The present invention is a totally enclosed fluid system having continuous or intermittent fluid flow. The invention provides an enclosed fluid system that is resistant to contamination by microorganisms resulting from the formation of biofilm and, in particular, eliminates the growth of microorganisms, such as bacteria and any associated biofilm, within the enclosed fluid system. The invention also provides a totally enclosed fluid system that is resistant to contamination by microorganisms and that may be used in both residential and commercial settings. In a most basic form, the enclosed fluid system comprises a point of fluid entry, a point of fluid exit, and system components that are intermediately positioned between the point of fluid entry and the point of fluid exit, including but not limited to fluid filters, fluid circulation members, fluid treatment members and fluid storage members. Each of the system components comprise fluid contacting portions that are made of polymers or a polymer composite material.

The invented enclosed fluid system prevents or minimizes the formation of biofilm within the fluid system by incorporating an antimicrobial agent, such as 2,4,4'-trichloro-2'-hydroxy diphenol ether, or 5-chloro-2-phenol (2,4-dichlorophenoxy) commonly sold under the trademark MICROBAN® Additive B by Microban Products Company of Huntersville, North Carolina, into the polymeric components that make up and or line the system.

Figure 1:
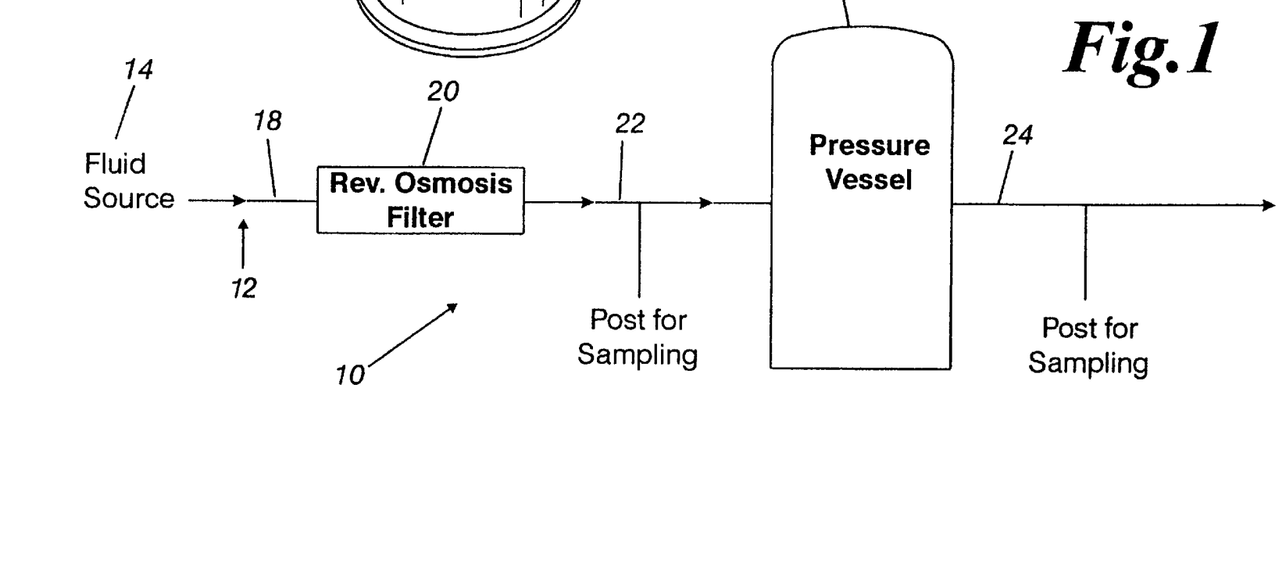
FIG. 1 is a schematic diagram of a totally enclosed fluid system including a fluid filter and a fluid storage tank in accordance with one embodiment of the present invention.

Referring now to the drawings, FIG. 1 is a schematic representation of an enclosed fluid system, shown generally at 10, including a fluid filter 20 and a fluid storage tank 30 in accordance with one embodiment of the present invention. One example of an enclosed fluid system is a water system for a residential application. Fluid is introduced to the invented system 10 at the point of fluid entry 12 of a fluid entry member from a fluid source 14, such as a well or a municipal distribution outlet, and travels through a conduit 18, or piping, to the filter 20. The fluid source 14 may be a single source that is connected to the point of fluid entry 12 or multiple sources that are all connected to the point of fluid entry 12. The conduits 18 comprises at least one pipe and is dependent on the desired characteristics of the enclosed fluid system 10. For example, if the enclosed fluid system 10 has multiple storage members, circulating members or fluid treatment members, the conduits 18 have an appropriate number of pipes to route desired fluid connections from one system component to another system component. The piping 18 is typically made from a polymer or copolymer that is selected from the group comprising of: polyolefin, epoxies, polyethylene, polyurethane, polypropylene, polyvinyl chloride, acrylonitrile butadiene styrene, polystyrene, polycarbonate, polyvinylidene fluoride, polyacrylate, polymethyl methacrylate, isoprene, styrene butadiene rubber, butyl rubber, polyurethane, silicone, polybutylene, polybutylene terephthalate, polyether sulfone, polyphenyllenoxide, polyphenylene ether, polyphenylene sulfide, polyphtatamide, polysulphene, polyester, nylons, fluoropolymers, and other combinations of polymers. For purposes of this discussion the terms polymer, copolymer and plastic are used interchangeably.

The filter 20 removes dissolved salts particles from the fluid and may be any conventional fluid filter type depending on the quality of the fluid source. The filter 20 is preferably a reverse osmosis type fluid filter such as those described in U.S. Pat. Nos. 5,762,797 and 5,868,933, both of which are incorporated herein by reference. Multiple filters may be used in the enclosed fluid system 10. For example, an additional filter (not shown) having carbon absorption units for removal of certain organic compounds or heavy metals may be used together with the reverse osmosis filter 20.

Fluid leaves the filter 20 and travels through additional piping 18 to a storage vessel 30. The storage vessel 30 may be an enclosed tank or any other conventional type of fluid storage device. The storage vessel 30 is preferably a pressurized fluid tank. In one embodiment, the interior of the pressurized fluid tank is lined with a polymer coating or contains a polymer liner that is coupled with a plastic diaphragm, such as a butyl diaphragm. The polymer liner and diaphragm separate the storage tank into two adjacent chambers: a fluid containing chamber; and, a biasing chamber. Storage tanks containing a diaphragm produce a pressurized flow of fluid therethrough by pressurizing the volume of the biasing chamber of the storage tank against the volume of the fluid containing chamber.

Figure 2:
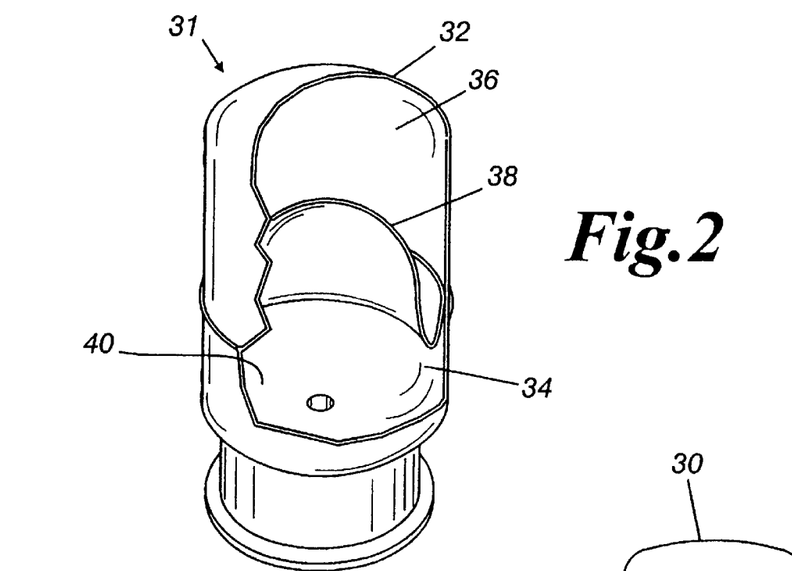
FIG. 2 is a diagram of a pressurized storage vessel showing a polymer lining and a diaphragm in accordance with one embodiment of the present invention.

A pressurized fluid storage envisioned for use in the system 10 is shown in FIG. 2. FIG. 2 is a diagram of a pressurized fluid storage vessel, or tank, shown generally at 31, showing a polymer lining 34 and an elastic diaphragm 38 in accordance with one embodiment of the present invention. The pressurized fluid tank 31 comprises an outer steel tank 32 that is separated into approximately two portions. A bottom portion 40 of the pressurized fluid tank 31 has the polymer lining 34 and is separated from an upper portion 36 of the tank 31 by the elastic diaphragm 38. The lining 34 is preferably made from a polymer or copolymer selected from the group comprising: epoxies, polyethylene, polyurethane, polypropylene, polyvinyl chloride, acrylonitrile butadiene styrene, polystyrene, polycarbonate, polyvinylidene fluoride, polyacrylate, polymethyl methacrylate, isoprene, styrene butadiene rubber, butyl rubber, polyurethane, silicone, polybutylene, polybutylene terephthalate, polyether sulfone, polyphenyllenoxide, polyphenylene ether, polyphenylene sulfide, polyphtatamide, polysulphene, polyester, nylons and fluoropolymers. The elastic diaphragm is made from a flexible plastic, such as butyl rubber, nitrile rubber, styrenebatadiene rubber, isoprene rubber, and polyurethane. In a preferred embodiment, the lining 34 is made of polypropylene and the lining 38 from butyl rubber.

When the fluid storage vessel 30 (FIG. 1) is a pressurized fluid tank 31, fluid that is filtered by the filter 20 enters the tank 31 through an inlet connection (not shown) and is stored in the bottom portion 40 of the tank. The upper portion 36 of tank 31 is kept under pressure by injecting compressed gas through a compressed gas port (not shown) provided in the upper portion 36 of the tank 31. The pressurized upper portion 36 of the tank 31 exerts force on the diaphragm 38 which in turn exerts pressure on the fluid that is stored in the bottom portion 40 of the tank 31, The result is a pressurized flow of fluid out of the tank 31 and into the pipes 18 that carry the fluid to a fluid exit point of the fluid exit member.

The invented enclosed system 10 described herein is protected from microbial contamination and proliferation by incorporating an antimicrobial agent into the fluid contacting portions of each component of the invented system 10. The use of components made of plastic to enclose, carry, filter and store the water provides a mechanism for incorporating an antimicrobial agent into the system components. To achieve the maximum amount of protection, all surfaces within the system that come into contact with water are preferably made of a polymer or coated with a polymer.

An antimicrobial agent, such as MICROBAN® Additive B, is incorporated into the fluid contacting portions of the system components by a technique of master batching that is well known to those versed in the art of plastic molding and formulations. For example, a range of about 10 to 50% by weight concentrate of MICROBAN® Additive B is prepared initially by mixing MICROBAN® Additive B in a hopper with pellets of a desired type of polymer or plastic. The mixture is then extruded at a temperature at which the desired plastic melts to a pre-determined consistency through a twin screw, intermeshing, counter-rotating extruder, such as one commercially sold under the name of "Leitritz". After the homogenized mixture is cooled, the mixture is pelletized having a desired, pre-determined concentration of antimicrobial agent. The antimicrobial agent in the form of the aforementioned pellets is added to additional polymer during subsequent extrusion or melt processing with a pre-determined ratio to achieve a specific final concentration of antimicrobial agent in the polymer while the polymer is in a molten stage and prior to the extrusion of the polymer. Upon cooling, the antimicrobial agent resides in the interstitial amorphous spaces of the polymer matrix.

An extremely small portion of this antimicrobial agent migrates continuously from the interstitial amorphous spaces of the polymer matrix to the surface of the polymer in order to maintain equilibrium of the interstitial concentration of the antimicrobial agent. The antimicrobial agent residing on the surface of the polymer prevents the growth of microorganisms thereon. In particular, it is discovered that MICROBAN® Additive B that is added at about 100 to 20,000 ppm and preferably added at about 1000 to 5000 ppm, depending on the application, controls the growth of most kinds of bacteria and fungi responsible for the formation of biofilm in water. Furthermore, MICROBAN® Additive B does not leach out in any significant quantities, is safe, non-toxic, non-carcinogenic, non-sensitizing to human and animal skin and does not accumulate in the human body when ingested.

EXAMPLES

Example 1

As an example of incorporation of an antimicrobial agent into an enclosed fluid system, a pressurized water tank was lined with a polymer lining. The polymer lining was made by first mixing pellets of MICROBAN® Additive B with polypropylene where the concentration of MICROBAN® Additive B was about 10% by weight. This mixture was then blow molded by further dilution to form a liner having a MICROBAN® Additive B concentration of about 5000 ppm and an approximately 20 mil thickness. The polypropylene was polypropylene Aristech #PPT14224G manufactured by Aristech Chemical Company.

An elastic diaphragm was formed in much the same way as the aforementioned polymer liner. A mixture of approximately 50% concentrate of MICROBAN® Additive B and talc was formed, and pre-cured butyl rubber was added to this mixture to form mixture having a final MICROBAN® Additive B concentration of about 2500 ppm. This mixture was then blow molded to form an elastic diaphragm having a final MICROBAN® Additive B concentration of approximately 2500 ppm and a thickness of approximately 100 mil.

The MICROBAN® Additive B treated diaphragm and liner of this Example 1 were tested for antimicrobial efficacy against Gram positive, namely Staphyloccus aureus, and Gram negative, namely Klebsiella pneumoniae, bacteria using American Association of Textile Chemists and Colorists (AATCC) Test Method 147-1993.

In Table 1, butyl diaphragms incorporating MICROBAN® Additive B and made in accordance with the present invention were incubated at about 37° C. for about 18 to 24 hours in a nutrient broth. In Table 2, a polypropylene liner incorporating MICROBAN® Additive B and made in accordance with the present invention was incubated at about 37° C. for about 18 to 24 hours in a nutrient broth. In Table 3, apolyethylene liner incorporating MICROBAN® Additive Band made in accordance with the present invention was incubated at about 37° C. for about 18 to 24 hours in a nutrient broth. Tables 1, 2 and 3 show that the respective diaphragms and liners that were made in accordance with the present invention have effective antimicrobial action because they deactivate the microorganisms that come in contact with the treated polymeric surfaces of the diaphragms and liners. Further, the treated polymeric surface has a zone of inhibition for the bacteria growth. These surfaces therefore resist the establishment of a biofilm thereon.

TABLE 1

Results (Zone Size)

| Sample | S. aureus | K. pneumoniae | E. coli |
|---|---|---|---|
| 5888-Steel RO tank diaphragm | 12 mm | 6 mm | 7 mm |
| 5889-Steel RO tank diaphragm | 12 mm | 7 mm | 7 mm |
| 5890-WX-104 diaphragm | 13 mm | 7 mm | 8 mm |

Interpretation of Results:
NZ=No Zone of inhibition surrounding the sample
NI=No Inhibition of Growth Under the Sample
I=Inhibition of Growth Under the Sample (If Observable)
mm=Zone of Inhibition Reported in Millimeters

TABLE 2

Results (Zone Size)

| Sample Identification | S. aureus | K. pneumoniae |
|---|---|---|
| 5068-WX-102 liner | 35 mm | 19 mm |

Interpretation of Results:
NZ=No Zone
NI=No Inhibition of Growth Under the Sample
I=Inhibition of Growth Under the Sample
mm=Zone of Inhibition Reported in Millimeters

TABLE 3

Results (Zone Size)

| Sample Identification | S. aureus | K. pneumoniae |
|---|---|---|
| 4837-WX-104 liner | 19 mm | 13 mm |
| 4839-Steel RO-4 tank liner | 22 mm | 15 mm |
| 4840-Hot water tank | 22 mm | 14 mm |

Interpretation of Results:
NZ=No Zone
NI=No Inhibition of Growth Under the Sample
I=Inhibition of Growth Under the Sample
mm=Zone of Inhibition Reported in Millimeters

Example 2

In Table 4, a test was performed to provide an indication of the antimicrobial characteristics of a polyurethane tube incorporating MICROBAN® Additive B and made in accordance with the present invention. A Modified Pour Plate Test utilizing columns of Mannitol salt agar was used. The pure agar, when solidified, has a deep red color. Upon inoculation of the organism Staphylococcus aureus, the agar turns yellow. The test was performed in culture tubes in which the agar was poured and allowed to partially solidify. Each of the tops of the agar columns were inoculated with the test organism. Immediately upon inoculation, the polyurethane tubes were pushed deep into the agar carrying test organisms with the tube. A utility knife was used to sharpen the end of the tubing in order to prevent the breaking of the media upon insertion of the tubing. Into one column, a polyurethane dental tubing containing approximately 20,000 ppm MICROBAN® Additive B was inserted. The other column received a control of untreated polyurethane dental tubing.

The dental tubing were incubated at about 37° C. and after approximately 18 hours, extreme yellowing of the agar (well over one half of the culture tube) was observed in the column housing the control, or untreated tubing. In the column containing the treated tubing, only a faint orange/yellow color was apparent near the very top of the agar column where the highest concentration of organisms were present. The rest of the column had a deep red color. This demonstrates that the exterior of the treated tubing has good antimicrobial efficacy.

Upon pushing the tubes into the agar columns, the agar was observed to have entered the lumen of the tubing. Inside the lumen of the nontreated control tubing, the agar appeared yellow just as the rest of the agar in the column. Inside the lumen of the treated tubing, the agar appeared just as the original deep red of the pure agar, indicating that the interior of the treated tube has good efficacy. Table 4 shows that the control tubing was not effective at inhibiting microbial growth whereas the treated tubing was significantly effective at inhibiting microbial growth. The treated tubing has effective antimicrobial control by deactivating the microorganisms that come in contact with the polymer surface of the treated tubing.

TABLE 4

Results (Zone Size)

| Sample Identification | S. aureus | K. pneumoniae |
|---|---|---|
| 4450-TPU Dental Tubing control | 1 | NZ/NI |
| 4451-TPU Dental Tubing 20,000 | 13 | 8 ppm |

Interpretation of Results:
NZ=No Zone
NI=No Inhibition of Growth Under the Sample
I=Inhibition of Growth Under the Sample
mm=Zone of Inhibition Reported in Millimeters

Example 3

Experiments were conducted to determine whether an antimicrobial agent could be successfully incorporated into a polyvinylidene fluoride (PVDF) pipe. A 10% concentrate of MICROBAN® Additive B was produced using Kynar® 720, manufactured by Elf Atochem, and a twin screw extruder in accordance with the present invention. The concentrate was subsequently diluted with additional Kynar® 720, homogenized and extruded to produce two PVDF pipes with concentrations of MICROBAN® Additive B of about 5000 ppm and about 10,000 ppm in accordance with the present invention. Table 5 shows the results of testing the PVDF tubing for antimicrobial efficacy using Kirby Bauer Test Method. The PVDF tubing incorporating MICROBAN® Additive B were incubated at about 37° C. for about 18 to 24 hours.

TABLE 5

Results (Zone Size)

| Sample Identification | S. aureus | K. pneumoniae |
|---|---|---|
| 6741-Sample A | 16 mm | 11 mm. |
| 6742-Sample B | 13 mm | 9 mm |

Interpretation of Results
NZ=No Zone of inhibitions surrounding the sample
NI=No Inhibition of Growth Under the Sample
I=Inhibition of Growth Under the Sample (If Observable)
mm=Zone of Inhibition Reported in Millimeters In Table 5, Sample A had about 10,000 ppm and Sample B had about 5,000 ppm of MICROBAN® Additive B. The results of Table 5 show that the PVDF tubing have significant antimicrobial properties.

Example 4

Three sizes of tubings were produced by Master Batch Technique in accordance with the present invention using Linear Low Density Polyethylene (LLDPE) and incorporating about 5000 ppm of MICROBAN® Additive B. The tubings were tested for antimicrobial efficacy using Kirby Bauer Test Method where the tubings were incubated at about 37° C. for about 18 to 24 hours. The results of these tubings are given in Table 6 which show that the treated LLDPE tubings have good efficacy against Gram positive, *S. aureus*, and Gram negative, *E. coli*, bacteria. Further the treated LLDPE tubings have a significant zone of inhibition of microbial growth.

TABLE 6

Results (Zone Size)

| Sample Identification (dimensions) | S. aureus | E. coli |
|---|---|---|
| 8198-#80224 (¼" × 0.171") | 20 mm | 14 mm |
| 8199-#80225 (0.312" × 0.156") | 17 mm | 14 mm |
| 8200-#80226 (0.465" × 0.265") | 20 mm | 13 mm |

Interpretation of Results:
NZ=No Zone of inhibition surrounding the sample
NI=No Inhibition of Growth Under the Sample
I=Inhibition of Growth Under the Sample (If Observable)
mm=Zone of Inhibition Reported in Millimeters

Example 5

Two types of tests were conducted on an enclosed system described in further detail herein below. The first test was intended to show that water storage tanks, having a diaphragm and a liner that have been treated with MICROBAN® Additive B in accordance with the present invention, will prevent the growth of biofilm in the storage space of the tank. Untreated tanks become a source of heterotrophic bacteria for the growth of bacterial biofilm in the tank. The second test, as described in greater detail in Example 6, determined the MICROBAN® Additive B concentration in the water that may result from leaching from the solid surfaces of the diaphragm and liner.

As previously mentioned, pressurized water storage tanks that are used in conjunction with reverse osmosis membrane modules, wells, and with hot water applications are subject to significant growth of biofilms. In addition to increasing the concentration of heterotrophic bacteria, sometimes to extremely high levels, biofilms impart taste and odor to the water. The present invention was tested to determine if treatment of the interior parts (liner and diaphragm) of pressurized water storage tanks with an antimicrobial MICROBAN® Additive B will prevent the growth of the biofilm on the water storage surfaces of the tank. In turn, the test of the present invention also determined whether the quality of water stored in the pressurized water storage tanks would be improved with respect to the presence of heterotrophic bacteria and other taste and odor effects associated with such bacteria. Another relevant part of this test involved the determination of the amount of antimicrobial agent that might have leached into the water stored in such tanks. If these concentrations were high enough and posed toxicological and long-term health risks, then the benefits of the antimicrobial treatment of the pressurized water storage tanks in accordance with the present invention may be negated.

Two types of tanks, both manufactured by Amtrol, were used. The first type was a Steel Tank-RO-4 that was used for water storage in conjunction with a reverse osmosis system. The other type was a Well-X-trol-WX-104 that was used in conjunction with a water well. Both of these tanks have polypropylene liners and butyl rubber diaphragms. MICROBAN® Additive B was incorporated into the liners and diaphragms during their manufacture in accordance with the present invention. The treated liners and diaphragms had a total MICROBAN® Additive B concentration of about 5000 ppm. Effectiveness of this treatment was confirmed by microbiological testing using AATCC Test Method 147-1993, for Gram positive bacteria, namely *S. aureus* (ATCC 6538), and Gram negative bacteria, namely *K. pneumoniae* (ATCC 4352) and Escherichia coli (ATCC 25922). The results of these evaluations were shown in previously mentioned in Tables 1, 2 and 3. These results confirm that the treated liners and diaphragms inhibit the growth of bacteria on the surface.

These liners and diaphragms that were used in fabricating Steel Tank-RO-4 and Well-X-Trol-WX-104 tanks were in turn used for the detection of biofilm formation and for leaching of MICROBAN® Additive B under the conventional usage. In this example, each Steel Tank-RO-4 was connected to a Watersoft-Clack TFC-25 D reverse osmosis membrane module containing a hydraulic pressure switch, and a water supply was connected to the reverse osmosis membrane module. The TFC-25 module was used as a source of heterotrophic bacteria. A first sampling port was located between the reverse osmosis membrane module and the RO-4 tank to analyze the influent, and a second sampling port was located after the RO-4 tank to analyze the effluent.

Tests for biofilm formation were carried out with the Amtrol RO-4 water storage tanks. Although simple in concept, determination of biofilm formation on a substrate is quite difficult to measure quantitatively. The static determinations require sacrificing the sample specimen to obtain either visual or microscopic examination. A dynamic method was devised using the principle that a biofilm, once formed, serves as a source of bacteria and increases the total count of the bacteria in the effluent over the count of bacteria in the influent.

A reverse osmosis membrane module commonly produces water with a certain concentration of heterotrophic bacteria, despite the manufacturer claims to the contrary. In this example, water is filtered through the reverse osmosis membrane module, and this water is then stored in the water storage tank. The air charge in each RO-4 tank creates a pressure of about 20 psi and a total water storage volume of about 3 gallons. When the pressure is lower than 30 psi, the hydraulic pressure switch opens and allows the fresh water to be processed through the reverse osmosis membrane module. Fresh water is processed until the storage tank pressure reaches about 50 psi filling the tank space completely with water when the pressure switch discontinues the water flow. Between each cycle of about 30 to 50 psi, the total water volume available is about 3 gallons.

Two replicate samples of storage tanks having MICROBAN® treated liners and diaphragms and an untreated control storage tank were each connected to a separate reverse osmosis membrane module having a hydraulic pressure switch. The units were operated every Monday, Tuesday, Thursday, and Friday by withdrawing and discarding about 2 gallons of water, and the storage tanks were completely emptied of water every Wednesday. Withdrawal of this water opens the hydraulic switch and allows processing of additional water through the reverse osmosis membrane module until the quantity of water in the storage tank is replaced. The Wednesday water sample was analyzed along with the influent sample obtained from the first sampling port, after appropriate dilutions, for heterotrophic bacteria. R2 media was used to determine bacterial count after incubating the water sample in the petri dish for about 24 hours at about 35° C. The bacterial count was expressed as Colony Forming Units (CFU) per cc of water. The bacterial analysis did not commence until day 24 to allow time for a significant number of CFU to develop. The experiment was continued over a period of 73 days to determine if the treated water storage tanks having water flow would prevent the formation of biofilm during actual operation, and the provided in Table 7.

TABLE 7

Heterotrophic Bacterial Count (CFU/ml) in Water before and after the Amtrol RO-4 Storage Tank.

| TIME | INFLUENT | | | EFFLUENT | | |
|---|---|---|---|---|---|---|
| Days | MB Tank 1 | MB Tank 2 | Control Tank | MB Tank 1 | MB Tank 2 | Control Tank |
| 24 | 6700 | 1500 | 1900 | 1100 | 410 | 9000 |
| 31 | 29000 | 5700 | 220 | 1500 | 710 | 13000 |
| 38 | 35000 | 5000 | 4400 | 2800 | 370 | 18000 |
| 45 | 8300 | 4900 | 2000 | 1200 | 470 | 11000 |
| 52 | 3600 | 4200 | 6100 | 1500 | 300 | 7900 |
| 59 | 49000 | 7000 | 6000 | 2000 | 300 | 13000 |
| 66 | 29000 | 5500 | 6200 | 7000 | 350 | 9000 |
| 73 | 14000 | 3000 | 6000 | 4000 | 250 | 19000 |

The results in Table 7 show that the effluent water leaving the untreated control tank consistently shows higher heterotrophic bacterial count compared to that in the influent water feeding the untreated control tank, thereby indicating the presence of biofilm. In contrast, the treated storage tanks show a decrease in the bacterial count when comparing the effluent water leaving the treated storage tanks with the influent water feeding the treated storage tanks. Some of the bacteria that come in contact with the treated surfaces of the liners and the diaphragms become deactivated. Thus, the results of Table 7 demonstrate that the treated liners and diaphragms prevent the formation of biofilm which acts as a source of bacteria and increases their count over the bacterial count present in the water introduced into the tank.

The results showed that MICROBAN Additive B treated water storage tanks prevented the formation of biofilm, as determined by the dynamic measurements on the heterotrophic bacteria in the influent and effluent samples. The treated tanks not only did not act as a source of heterotrophic bacteria, as would be expected to occur in the presence of a biofilm, but actually brought about the reduction in the total heterotrophic bacterial count of the water. With the residence time of the water in these storage tanks, sometimes in hours, the bacteria are expected to come in contact with the antimicrobial surfaces of the tank (liner, diaphragm) and become deactivated. This is also an indication that these surfaces will be hostile to the establishment of biofilm.

Example 6

Determining whether MICROBAN® Additive B was leached out of the treated liners and diaphragms and into the water was a very important and key objective of this test. MICROBAN® Additive B was incorporated into plastic polymers in the molten state while being extruded in accordance with the present invention. This results in a greater than 99.9% of MICROBAN® Additive B residing within the plastic article and only a very minute fraction of the additive residing on the surface of the plastic article. MICROBAN® Additive B that is incorporated into the polymer substrate and resides on the surface of the substrate is at equilibrium, but only the amount of additive on the surface is subject to quick leaching MICROBAN® Additive B is only sparingly soluble in water.

Manufacturers of water storage tanks recommend that when these tanks are idle for more than a day or two, that they should be completely emptied and refilled with freshly produced water from the reverse osmosis membrane module. Leaching of MICROBAN was evaluated under a worst case scenario and under the normal operating conditions.

The leaching tests were conducted using the aforementioned Steel Tank RO-4 configuration of Example 5 and with a Well-X-Trol WX-104. The Well-X-Trol WX-104 was connected to a pump which in turn was connected to a well. A sampling port was located after the WX-104 tank to analyze the effluent.

In the worst case scenario, water was allowed to remain in the Amtrol RO-4 tank for a period of a month and only a liter sample of water was withdrawn from the tank once a week. No other water was drawn from the storage tank and it remained full (at 50 psi) during this month long trial. The objective was to determine how much MICROBAN® Additive B concentration builds up in the stored water over a period of a month under stagnant conditions. This is a highly unlikely scenario as manufacturers require the storage tank to be completely emptied after about a 24 to 48 hour stagnancy, as previously mentioned.

In the second case, water from the Well-X-Trol tank attached to a well pump was tested. Here, the water turnover is rapid. An average family of four uses approximately 400 gallons per day of water from the well. At the rate of about 3–4 gallons per draw (depending on the size of the tank), there are usually about 50 cycles of evacuations and fillings per day from a well water storage tank. Under these conditions of constant use, water samples were taken over a period of 50 days and analyzed for MICROBAN® Additive B.

Analysis of the water for MICROBAN® Additive B was done using a gas chromatographic procedure including an Electron Capture Detector with an RTX-5 column or equivalent. The sample was prepared by extracting 250 ml of water with three (3) 25 ml aliquots of ISO-Octane. Three extracts were combined and concentrated to a 25 ml volume before injecting into the gas chromatograph. This concentration step controls the sensitivity of the analysis. In the past, the sensitivity was measurable to about 50 parts per billion. Currently, a sensitivity of 25 parts per billion has been achieved by the previously mentioned concentration step.

The results of the concentration of MICROBAN® Additive B in the water from Amtrol-RO-4 tanks are provided in Table 8 where samples were obtained from a month long stagnant condition. The results of the concentration of MICROBAN® Additive B in the water from Well-X-Trol WX-104 tanks are provided in Table 9 where samples were obtained from a routine turnover from the water storage tank installed on a well.

Under the stagnant conditions (Table 8), the concentration of MICROBAN® Additive B increased at a rate of about 25 parts per billion per week. The sample of water withdrawn each week was only about 1 liter in a total water volume of 3 gallons. The withdrawn volume was immediately replaced by fresh water from the reverse osmosis membrane module. These results show that there is no significant increase in the concentration of MICROBAN® Additive B under the extreme stagnant conditions and, therefore, the additive as incorporated into the tank poses no toxicological or health risk. These test conditions are extremely unlikely under the normal operating conditions.

TABLE 8

| Sample | Date (Parts per billion) | | | |
| --- | --- | --- | --- | --- |
| | July 22 | July 29 | August 5 | August 12 |
| Amtrol RO-4 | 23.6 | 56.8 | 75.0 | 98.2 |

Under the conditions of normal turnover, as best shown in Table 9, the concentration of MICROBAN® Additive B never exceeded about 25 parts per billion. Both of the above results are significant indicators of the safety of treating water storage tanks with MICROBAN® Additive B.

The amount of MICROBAN® Additive B found in the water through dissolution was negligible. Under the normal operating conditions of the invented system, less than 25 parts per billion of this antimicrobial agent can be expected in the water. Under prolonged stagnant conditions, this concentration is expected to reach about 100 parts per billion after a month of stagnation. This latter condition is highly unlikely as the manufacturers of water storage tanks strongly recommend a complete emptying of these tanks after a 24 to 48 hour idle period when the water is not being drawn. Treatment of these storage tanks with MICROBAN® Additive B prevents the formation of biofilm and improves the quality of the water without posing any toxicological or health risks.

TABLE 9

| Sample (date withdrawn) | Result |
| --- | --- |
| Sample: Water 1-10/22/98 | <25 ppb |
| Sample: Water 2-10/28/98 | <25 ppb |
| Sample: Water 3-11/4/98 | <25 ppb |
| Sample: Water 4-11/18/98 | <25 ppb |
| Sample: Water 5-12/10/98 | <25 ppb |

Example 7

A dental tubing sample was qualitatively analyzed for MICROBAN® Additive B content. The analysis was done by dissolving a known amount of the tubing sample in 9 milliliters of dimethyl formamide and precipitating out the thermoplastic polyurethane (TPU) with methanol. The methanol/MICROBAN® Additive B extract was then analyzed by gas chromatography using an electron capture detector. One microliter was injected in the sample and the analysis was conducted isothermally at about 250 degrees Celsius. The digestion data and results are provided in Table 10. The qualitative results in Table 10 indicate that MICROBAN® Additive B was incorporated into the tubing.

ALTERNATIVE EMBODIMENTS

TABLE 10

| Sample | Sample Mass (g) | Extracted MICROBAN B Content (ppm) |
| --- | --- | --- |
| Dental Tubing | .1737 | 14,963.7 ppm |

One embodiment of the invention is represented by a totally enclosed water system utilized in dentist chairs. Dentist chairs are often self-contained units that filter, store and transport purified water to a patient through plastic tubing. A plastic tubing suitable for use in dental chairs is produced in a manner similar to that described above for the plastic diaphragms and liners. In this application, a polyurethane tube containing approximately 20,000 ppm of MICROBAN® Additive B is formed from Pellethane 2103-90AEN, which is manufactured by Dow Plastics. The aforementioned Table 4 confirms the ability of this polyurethane dental tubing to inhibit the growth of Gram positive and Gram negative bacteria.

The present invention provides a method of minimizing and preventing the growth of biofilm on antimicrobial coated metal surfaces for an enclosed water system that inhibits the growth of biofilm and improves the quality of the water without significant toxicological or health risks. The method includes the steps of a providing a point of fluid entry into the totally enclosed fluid system, providing a point of fluid exit, and connecting fluid circulation and fluid storage members intermediate between the point of fluid entry and the point of fluid exit, the fluid circulation and fluid storage members having internal surfaces. The step of coating the internal surfaces with polymers includes incorporating a non-leaching antimicrobial agent on and within the internal surfaces of the fluid circulation and fluid storage members so that the agent inhibits the growth of microorganisms at all points within the totally enclosed fluid system from the point of fluid entry to the point of fluid exit. The incorporating step further includes providing a non-leaching antimicrobial additive selected from the group consisting of 2,4,4'- trichloro-2'-hydroxy diphenol ether and 5-chloro-2-phenol (2,4-dichlorophenoxy). The polymers utilized in the coating step are selected from the group consisting of epoxies, polyethylene, poloypropylene, polyvinyl chloride, polyvinyl chloride/nitrile, chlorobutyl, acrylonitrile butadiene styrene, polystyrene, polycarbonate, polyvinylidene fluoride, polyacrylate, polymethyl methacrylate, isoprene, stryrene butadiene rubber, butyl rubber, polyurethane, silicone, polybutylene, polyester, nylons, polybutylene, polybutylene terephthalate, polysulfone, polyphenyllenoxide, polyphenylene ether, polyphenylene ether, polypheylene sulfide, polyphtatamide, polysulphene, fluoropolymers, and copolymers of the polymers.

SUMMARY OF THE ACHIEVEMENT OF THE OBJECTS OF THE INVENTION

From the foregoing, it is readily apparent that I have invented an apparatus for preventing microbial growth in an enclosed fluid system comprising a point of fluid entry and a point of fluid exit. Between the point of fluid entry and the point of fluid exit are fluid circulation members, valves, fluid treatment members and fluid storage members. In one embodiment of the invention, a non-leaching antimicrobial agent that inhibits the growth of microorganisms is incorporated into all components of the system that are in contact with the fluid. Therefore, from the time the fluid enters the system until the fluid exits the system, the fluid is contained within an enclosed space formed of material that incorporates an antimicrobial agent. The enclosed antimicrobial fluid system provides for reduction of the growth of microbial contamination and proliferation within the fluid in and passing through the system, without significant leaching in the fluid.

It is to be understood that the foregoing description and specific embodiments are merely illustrative of the best mode of the invention and the principles thereof, and that various modifications and additions may be made to the apparatus by those skilled in the art, without departing from the spirit and scope of the appended claims.

What is claimed is:

1. An enclosed antimicrobial fluid system comprising:
    a fluid entry member having a point of fluid entry and a fluid contacting portion;
    a fluid exit member having a point of fluid exit and a fluid contacting portion;
    at least one intermediate member interconnecting said point of fluid entry and said point of fluid exit, said at least one intermediate member having a fluid contacting portion; and
    a non-leaching antimicrobial agent incorporated into each of said fluid contacting portion of said fluid entry member, said fluid contacting portion of said at least one intermediate member and said fluid contacting portion of said fluid exit member;
    wherein said antimicrobial agent inhibits the growth of microorganisms at the fluid contacting portions within the system from said point of fluid entry through said point of fluid exit.

2. An antimicrobial fluid system in accordance with claim 1 wherein said at least one intermediate member is selected from the group consisting of a fluid circulation member, a fluid storage member and a fluid treatment member.

3. An antimicrobial fluid system in accordance with claim 2 wherein said fluid treatment member is a mechanical fluid treatment member.

4. An antimicrobial fluid system in accordance with claim 2 wherein said fluid treatment member is a fluid filter.

5. An antimicrobial fluid system in accordance with claim 1 wherein the antimicrobial agent is selected from the group consisting of 2,4,4-trichloro-2-hydroxy diphenol ether or 5-chloro-2-phenol (2,4, dichlorophenoxy) compounds.

6. An antimicrobial fluid system in accordance with claim 1 wherein said fluid contacting portion of said fluid entry, said fluid contacting portion of said fluid exit and said fluid contacting portion of said at least one intermediate member comprises a polymer selected from the group consisting of epoxy, polyethylene, polypropylene, polyvinyl chloride, polyvinyl chloride/nitrile, chlorobutyl, acrylonitrile butadiene styrene, polystyrene, polycarbonate, polyvinylidene fluoride, polyacrylate, polymethyl methacrylate, isoprene, styrene butadiene rubber, butyl rubber, polyurethane, silicone, polybutylene, polyester, nylons, polyethylene terephthalate, polybutylene terephthalate, polyether ether ketone, polyether sulfone, polyphenylleneoxide, polyphenylene ether, polypheylene sulfide, polyphtatamide, polysulphene, polytetrafluoroethylene and fluoropolymer.

7. An antimicrobial fluid system in accordance with claim 1 wherein said at least one intermediate member is selected from the group consisting of depth filter, reverse osmosis membrane module, pressure vessel, plastic tubing, metal tubing, plastic pipe and metal pipe.

8. An antimicrobial fluid system in accordance with claim 1 wherein said at least one intermediate member is a fluid storage member.

9. An antimicrobial fluid system in accordance with claim 8 wherein said fluid storage member comprises:
    an enclosed tank made of a metal selected from the group consisting of steel and stainless steel;
    an elastic diaphragm positioned within said enclosed tank, said elastic diaphragm dividing the interior of said enclosed tank into a fluid containing chamber and a biasing chamber; and
    a lining attached to the interior of said enclosed tank;
    wherein said fluid contacting portion of said fluid storage member includes said lining in said fluid containing chamber of said enclosed tank and said elastic diaphragm.

10. An antimicrobial fluid system in accordance with claim 9 wherein said lining of said fluid storage member is made of a polymeric material selected from the group consisting of epoxy, polyethylene, polypropylene, polyvinyl chloride, polyvinyl chloride/nitrile, chlorobutyl, acrylonitrile butadiene styrene, polystyrene, polycarbonate, polyvinylidene fluoride, polyacrylate, polymethyl methacrylate, isoprene, styrene butadiene rubber, butyl rubber, polyurethane, silicone, polybutylene, polyester, nylons, polyethylene terephthalate, polybutylene terephthalate, polyether ether ketone, polyether sulfone, polyphenyllenoxide, polyphenylene ether, polyphenylene sulfide, polyphtatamide, polysulphene, polytetrafluoroethylene and fluoropolymer.

11. An antimicrobial fluid system in accordance with claim 9 wherein said elastic diaphragm is made of a flexible plastic material selected from the group consisting of butyl rubber and polyurethane.

12. A method of inhibiting the growth of microorganisms in an enclosed fluid system comprising a point of fluid entry having a fluid contacting portion, a point of fluid exit having a fluid contacting portion and at least one intermediate member having a fluid contacting portion interconnecting the point of fluid entry and the point of fluid exit, said method comprising:
    selecting at least one intermediate member for coupling between the point of fluid entry and the point of fluid exit;
    incorporating a non-leaching antimicrobial agent into the fluid contacting portions of the point of fluid entry, the point of fluid exit and each of the selected intermediate members; and
    forming an enclosed fluid circulation and storage system that inhibits the growth of microorganisms at all fluid contacting surfaces within the system from the point of fluid entry to the point of fluid exit.

13. A method according to claim 12 wherein prior to said step of incorporating, said method further comprises:
    selecting an antimicrobial additive from the group consisting of 2,4,4'-trichloro-2'-hydroxy diphenol ether and 5-chloro-2 phenol (2,4-dichlorophenoxy).

14. A method according to claim 12 wherein after said step of selecting, said method further comprises:

selecting a liner for said intermediary member from the group consisting of epoxies, polyethylene, polypropylene, polyvinyl chloride, polyvinyl chloride/nitrile, chlorobutyl, acrylonitrile butadiene styrene, polystyrene, polycarbonate, polyvinylidene fluoride, poly acrylate, polymethyl methacrylate, isoprene, styrene butadiene rubber, butyl rubber, polyurethane, silicone, polybutylene, polyester, nylons, polyethylene terephthalate, polybutylene terephthalate, polyether ether ketone, polyether sulfone, polysulfone, polyphenylleneoxide, polyphenylene ether, polypheylene sulfide, polyphtatamide, polysulphene, polytetrafluorethylene and fluoropolymers.

\* \* \* \* \*